United States Patent
Knutzen et al.

(10) Patent No.: US 11,911,311 B2
(45) Date of Patent: Feb. 27, 2024

(54) DENTAL GUARD

(71) Applicant: Dentek Oral Care, Inc., Maryville, TN (US)

(72) Inventors: Josef V. Knutzen, Allendale, NJ (US); Jessica Rica Lin, Bayside, NY (US); Joseph R. Martone, Bristol, CT (US)

(73) Assignee: DENTEK ORAL CARE, INC., Tarrytown, NY (US)

( * ) Notice: Subject to any disclaimer, the term of this patent is extended or adjusted under 35 U.S.C. 154(b) by 0 days.

(21) Appl. No.: 17/031,722

(22) Filed: Sep. 24, 2020

(65) Prior Publication Data

US 2022/0087854 A1   Mar. 24, 2022

(51) Int. Cl.
A61F 5/56   (2006.01)

(52) U.S. Cl.
CPC ........ *A61F 5/566* (2013.01); *A61F 2005/563* (2013.01)

(58) Field of Classification Search
CPC ...... A61F 5/566; A61F 5/56; A61F 2005/563; A61C 5/14; A61C 3/00; Y10T 29/49826; B23P 17/04; A63B 71/08; A63B 71/085
USPC ................. 128/848, 859, 861, 862
See application file for complete search history.

(56) References Cited

U.S. PATENT DOCUMENTS

| | | |
|---|---|---|
| 2,257,709 A | 9/1941 | Anderson |
| 2,643,652 A | 6/1953 | Cathcart |
| 4,063,552 A | 12/1977 | Going et al. |
| 5,616,027 A | 4/1997 | Jacobs et al. |
| D406,405 S | 3/1999 | Yoshida |

(Continued)

FOREIGN PATENT DOCUMENTS

KR   102098391   4/2020

OTHER PUBLICATIONS

Amazon.com; Article entitled: "Armor Guard—1 Set Upper and Lower Custom Made Dental Lab with 40 Years of Experience, Mouth or Dental Guards, Day or Night, Teeth Clenching or Grinding, Multi-Symptom TMJ Bruxism Relief," located at <https://www.amazon.com/Armor-Guard-Clenching-Grinding-Multi-Symptom/dp/B018L8WPJG>, dated Apr. 21, 2020, 2 pages.

(Continued)

*Primary Examiner* — Alireza Nia
*Assistant Examiner* — Daniel A Miller
(74) *Attorney, Agent, or Firm* — Taylor English Duma LLP

(57) ABSTRACT

A dental guard for treatment of bruxism in a human dental arch. The dental guard comprises an elastically deformable body having a front band portion and a pair of molar portions contiguous with and extending from the ends of the front band portion. The distance between distal ends of the molar portions is configured to differ from the width of the human dental arch. The front band portion and molar portions form a U-shape configured and may have less curvature than a curvature of the human dental arch. The body includes a front side wall and an upper side wall extending at an angle from a longitudinal edge of the front side wall. The body is adapted to be positioned to fit over a plurality of teeth such that the inner surfaces of the front wall and the upper wall engage occlusal surfaces of the posterior teeth. When the jaws are closed the body at least partially conforms to the outer surfaces and occlusal surfaces of differently sized and differently shaped teeth corresponding to different people during use.

24 Claims, 13 Drawing Sheets

(56) References Cited

U.S. PATENT DOCUMENTS

| | | | |
|---|---|---|---|
| 6,302,110 B1 * | 10/2001 | Yoshida | A61F 5/566 128/862 |
| 6,860,736 B2 | 3/2005 | Allred et al. | |
| 7,048,543 B2 | 5/2006 | Allred et al. | |
| 7,052,275 B2 | 5/2006 | Allred et al. | |
| 7,192,280 B2 | 3/2007 | Allred et al. | |
| D548,402 S | 8/2007 | Trodick | |
| 7,882,839 B2 | 2/2011 | Ambis, Jr. | |
| 8,007,277 B2 * | 8/2011 | Fischer | A61C 19/063 433/80 |
| 8,196,587 B2 | 6/2012 | Chodorow | |
| D688,832 S | 8/2013 | Polk, III | |
| 8,667,971 B2 | 3/2014 | Makkar et al. | |
| D710,506 S | 8/2014 | Tolentino et al. | |
| 8,944,819 B2 * | 2/2015 | Faasse | A61C 19/063 424/53 |
| 8,956,160 B2 | 2/2015 | Willison et al. | |
| 9,199,120 B2 | 12/2015 | Hutchison | |
| D760,441 S | 6/2016 | Cody | |
| 9,642,739 B2 | 5/2017 | Schlatter | |
| 9,949,809 B2 | 4/2018 | Lewis et al. | |
| D821,036 S | 6/2018 | Mahoney | |
| D830,640 S | 10/2018 | Supple | |
| D833,621 S | 11/2018 | Tolentino | |
| D838,051 S | 1/2019 | Campanella | |
| D869,658 S | 12/2019 | Chodorow | |
| D874,654 S | 2/2020 | Martone et al. | |
| 10,913,853 B2 | 2/2021 | Johnson et al. | |
| D958,995 S | 7/2022 | Knutzen et al. | |
| 2006/0099550 A1 * | 5/2006 | Faasse | A61C 19/063 433/215 |
| 2009/0165805 A1 | 7/2009 | Syrop et al. | |
| 2011/0171606 A1 | 7/2011 | Lewis et al. | |
| 2012/0298118 A1 * | 11/2012 | Hutchison | A63B 23/032 128/862 |
| 2013/0291874 A1 | 11/2013 | Engel | |
| 2014/0238419 A1 | 8/2014 | Lovat | |
| 2014/0261464 A1 | 9/2014 | Layzell | |
| 2015/0305918 A1 | 10/2015 | Chodorow et al. | |
| 2015/0366700 A1 | 12/2015 | Choi et al. | |
| 2016/0175137 A1 | 6/2016 | Karni | |
| 2016/0230007 A1 | 8/2016 | Johnson et al. | |
| 2017/0001095 A1 * | 1/2017 | Lovat | A63B 71/085 |
| 2019/0117442 A1 | 4/2019 | Chodorow | |
| 2020/0061440 A1 | 2/2020 | Knutzen | |
| 2021/0115254 A1 | 4/2021 | Johnson et al. | |

OTHER PUBLICATIONS

Amazon.com; Article entitled "Reejoys Mouth Guard for Grinding Teeth, Custom Dental Night Guards for Teeth Grinding, Stops Bruxism Tmj & Eliminates Teeth Clenching," located at <https://www.amazon.com/Reejoys-Grinding-Bruxism-Eliminates-Clenching/dp/B07QNZJKSS>, dated Apr. 21, 2020, 2 pages.

Knutzen, Josef V.; Notice of Allowance for Design U.S. Appl. No. 29/752,083, filed Sep. 24, 2020, dated Mar. 14, 2022, 17 pgs.

\* cited by examiner

DENTAL GUARD

BACKGROUND

A dental guard is described and, more particularly, a dental guard for protecting against and treatment of bruxism.

Bruxism refers to excessive grinding and clenching of the teeth, especially at night. A person who suffers from bruxism is referred to as a bruxer.

A treatment for bruxism includes a custom-fitted plastic mouth appliance, or dental guard, which is worn at night to absorb the force of biting and grinding of the teeth. The dental guard is intended to reduce damage to the teeth and reduce the noise associated with bruxing or grinding by minimizing abrasion of tooth surfaces. The dental guard is obtained through visits to a dentist for measuring and fitting. The fitted dental guard is initially designed to the shape of an individual's upper teeth or lower teeth from a bite mold. This is a time consuming and expensive process.

For the foregoing reasons, there is a need for a non-custom dental guard for protecting against bruxism and nighttime teeth grinding. The new dental guard should approximate the shapes and sizes of a variety of dental arches and should be capable of fitting mouths which differ substantially in size from one another within a wide range. Ideally, the dental guard will accommodate the range of mouth sizes regardless of teeth characteristics.

SUMMARY

A dental guard is provided for treatment of bruxism in a human dental arch including a plurality of anterior teeth and posterior teeth having outer surfaces and occlusal surfaces. The dental guard comprises an elastically deformable body having a front band portion and a pair of molar portions contiguous with and extending from ends of the front band portion to distal ends of the pair of molar portions. The distance between the distal ends of the pair of molar portions is configured to differ from the width of the human dental arch. The front band portion and the pair of molar portions form a U-shape configured to have less curvature than a curvature of the human dental arch. The body includes a front side wall having an inner surface, and an upper side wall having an inner surface and extending at an angle from a longitudinal edge of the front side wall. The body is adapted to be positioned to fit over the plurality of teeth of the human dental arch such that the inner surfaces of the front wall and the upper wall engage the occlusal surfaces of the posterior teeth. When the jaws are closed the body at least partially conforms to the outer surfaces and occlusal surfaces of differently sized and differently shaped teeth corresponding to different people during use.

In one embodiment, the dental arch comprises the lower dental arch and the teeth are lower teeth. In another embodiment, the dental arch comprises the upper dental arch and the teeth are upper teeth.

In one embodiment, the distance between the distal ends of the pair of molar portions is less than the width of the human dental arch. In another embodiment, the distance between the distal ends of the pair of molar portions is greater than the width of the human dental arch.

In one aspect, a portion of the front side wall corresponding to the front band portion is a labial wall disposed between the outer surfaces of the anterior teeth and the inside surface of the lip, and the front side wall of each of the molar portions comprises a buccal wall contiguous with the labial wall. The buccal wall disposed between the outer surfaces of the posterior teeth and inside surfaces of the cheeks.

In another aspect, the labial wall terminates in a longitudinal free edge positioned adjacent a gingival margin during use, and the buccal wall is adapted to overlap a junction of a person's gingival margin/gum line during use.

The body of the dental guard may have a thickness of from about 0.2 mm to about 4 mm, or from about 0.4 mm to about 2 mm, or from about 0.6 mm to about 0.9 mm. In one embodiment, the body has a thickness of less than about 1.0 mm.

In yet another aspect, the upper side wall of each molar portion comprises a generally planar occlusal plate having top and bottom surfaces adapted to be positioned between the facing occlusal surfaces of upper teeth and lower teeth to absorb forces when the jaws are clenched. Moreover, the width of the upper side wall gradually increases from the front band portion to the molar portions. In one embodiment, the width of the upper side wall of the molar portions may be about 8 mm in a direction generally perpendicular to longitudinal axis of the front wall.

In a further aspect, the body of the dental guard has a transverse cross section that is approximately V-shaped, and the body is adapted to extend along the dental arch to substantially cover the outer surfaces and crowns of the teeth to the distal end of the second molar of the lower dental arch. The longitudinal edge of the front wall may be in substantially the same plane, and the distance between the distal ends of the pair of molar portions is dimensionally stable in the plane.

A method for protecting against effects of bruxism in a subject is also provided. The bruxism protection method comprises the steps of providing an elastically deformable body having a front band portion, and a pair of molar portions contiguous with and extending from the ends of the front band portion to distal ends of the pair of molar portions. The distance between the distal ends of the pair of molar portions is configured to differ from the width of a human dental arch, with the front band portion and the pair of molar portions forming a U-shape. The body includes a front side wall having an inner surface, and an upper side wall having an inner surface. The upper side wall extends at an angle from a longitudinal edge of the front side wall. The method further comprises the steps of placing the body over a plurality of teeth in the human dental arch such that the inner surfaces of the front wall and the upper wall engage the occlusal surfaces of the posterior teeth, and conforming the body to the teeth and surrounding tissue by dental pressure so that when the jaws are closed the body at least partially conforms to the outer surfaces and occlusal surfaces of differently sized and differently shaped teeth corresponding to different people during use.

In one embodiment, the dental arch comprises the lower dental arch and the teeth are lower teeth. In another embodiment, the dental arch comprises the upper dental arch and the teeth are upper teeth.

In one embodiment, the distance between the distal ends of the pair of molar portions is less than the width of the human dental arch. In another embodiment, the distance between the distal ends of the pair of molar portions is greater than the width of the human dental arch.

A kit is also provided for use in protecting a person's teeth, the kit comprising a plurality of the dental guards as described herein.

BRIEF DESCRIPTION OF THE DRAWINGS

For a more complete understanding of the dental guard, reference should now be had to the embodiments shown in the accompanying drawings and described below. In the drawings.

DESCRIPTION

Figure 1:
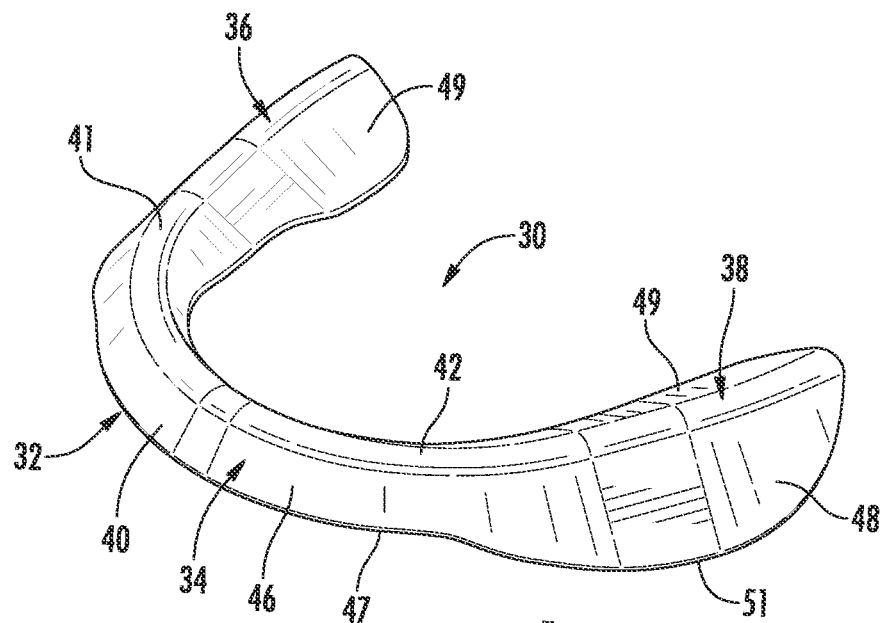
FIG. 1 is a top front left side perspective view of an embodiment of a dental guard.
Figure 2:
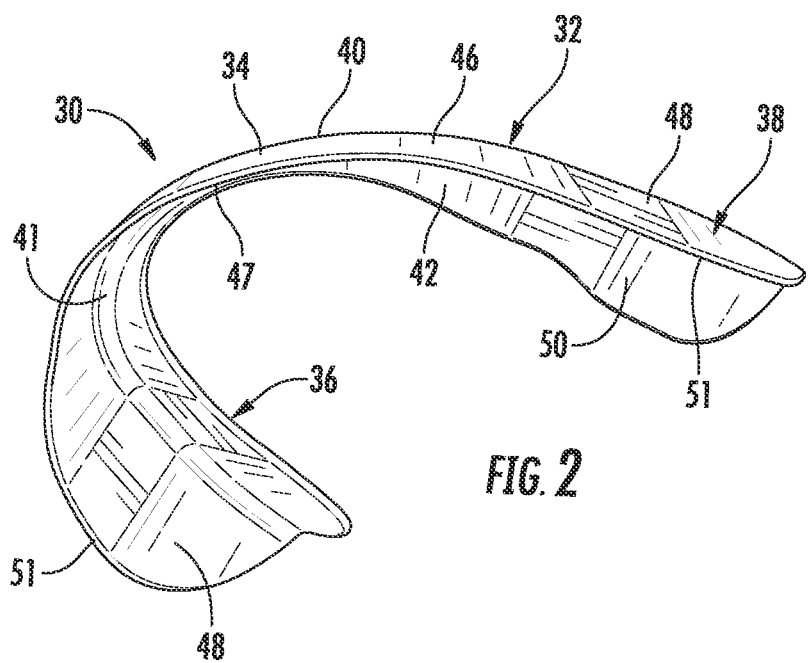
FIG. 2 is a bottom front left side perspective view of the dental guard as shown in FIG. 1.
Figure 3:
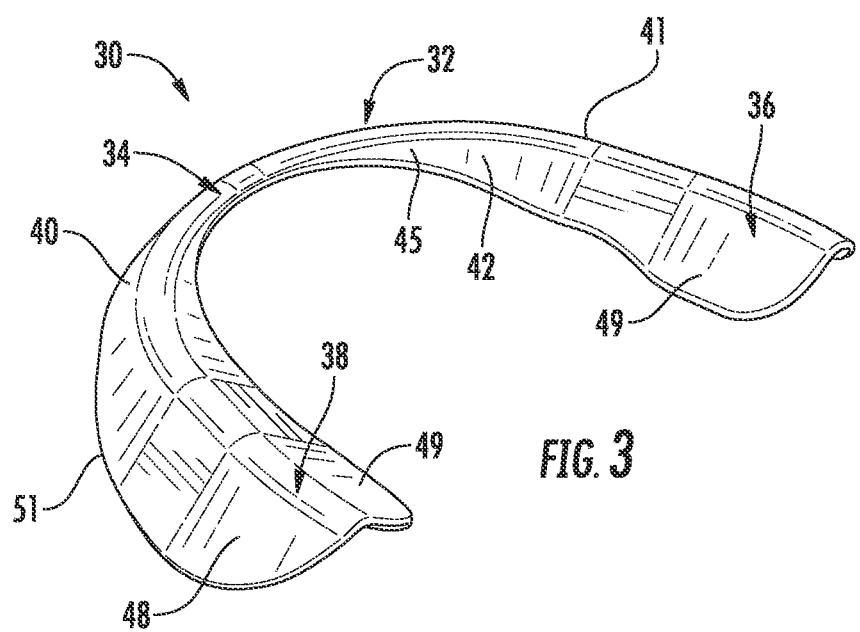
FIG. 3 is a top rear left side perspective view of the dental guard as shown in FIG. 1.
Figure 4:
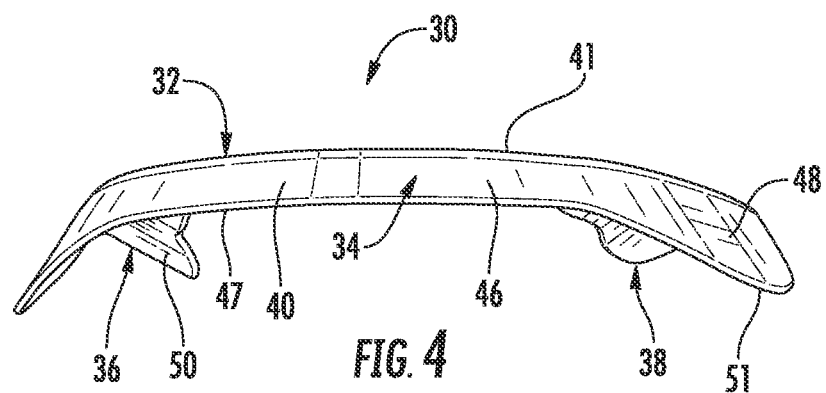
FIG. 4 is a bottom front perspective view of the dental guard as shown in FIG. 1.
Figure 5:
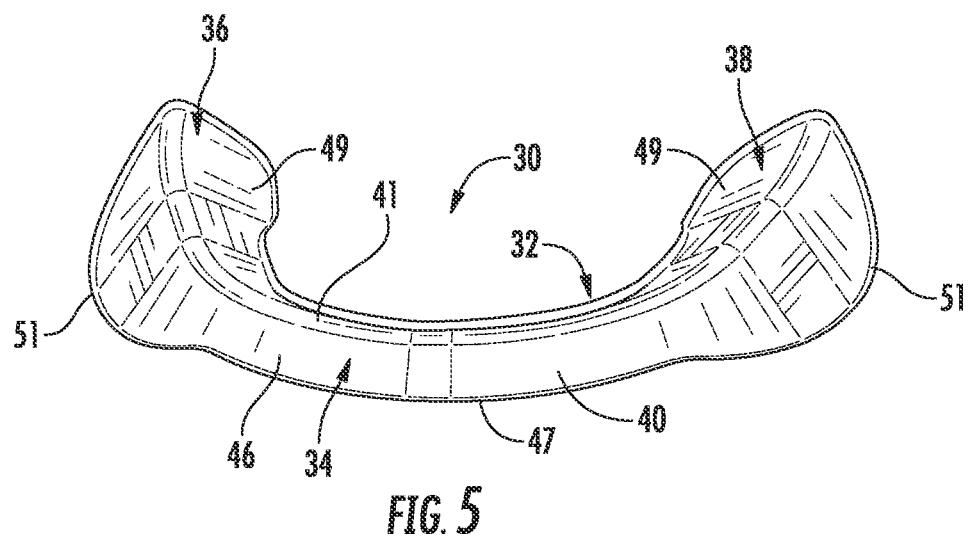
FIG. 5 is a top front perspective view of the dental guard as shown in FIG. 1.
Figure 6:
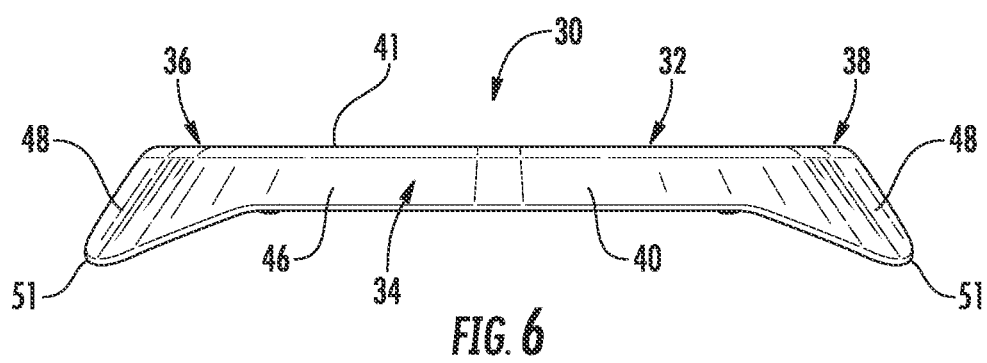
FIG. 6 is a front elevation view of the dental guard as shown in FIG. 1.
Figure 7:
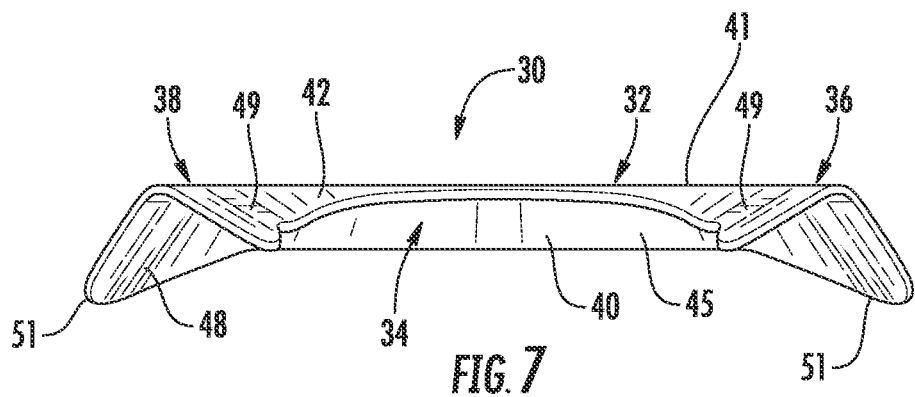
FIG. 7 is a rear elevation view of the dental guard as shown in FIG. 1.
Figure 8:
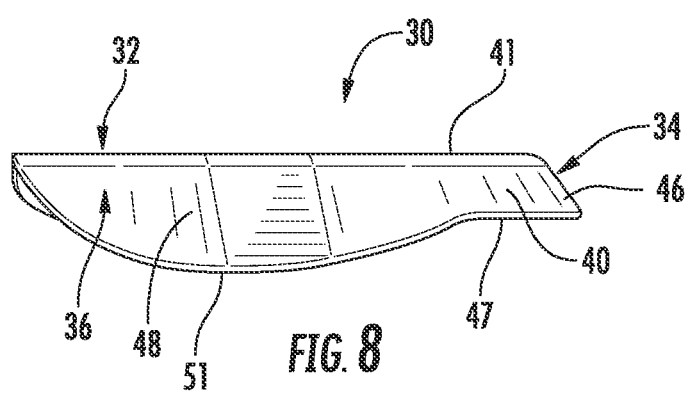
FIG. 8 is a right side elevation view of the dental guard as shown in FIG. 1.
Figure 9:
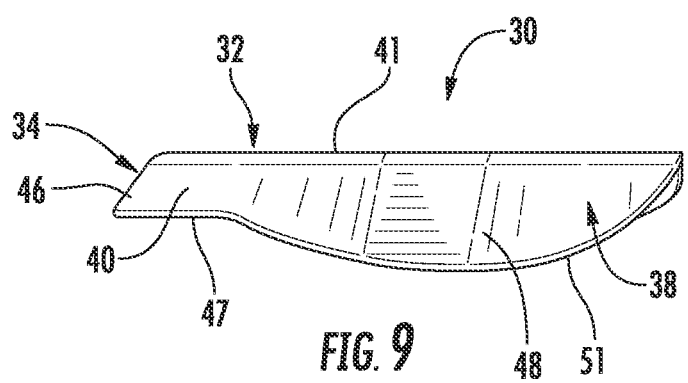
FIG. 9 is a left side elevation view of the dental guard as shown in FIG. 1.

Certain terminology is used herein for convenience only and is not to be taken as limiting. For example, words such as "upper," "lower," "left," "right," "horizontal," "vertical," "upward," "downward," "top" and "bottom" merely describe the configurations shown in the drawings. Indeed, the components may be oriented in any direction and the terminology, therefore, should be understood as encompassing such variations unless specified otherwise. The words "interior" or "inner" and "exterior" or "outer" refer to directions toward and away from, respectively, the geometric center of the core and designated parts thereof. The terminology includes the words specifically mentioned above, derivatives thereof and words of similar import.

An adult human will typically have a permanent dentition composed of sixteen teeth in an upper dental arch and sixteen teeth in a lower dental arch. As used herein, "dental arch" means an individual row of teeth forming a tooth row attached to either the upper or lower jaw bone. The curve of the dental arch is known as the catenary arch. Each dental arch has the following tooth types arranged symmetrically in the arch: four incisors or front teeth, two canines, four bicuspids and six molars. The incisors and canines are called the anterior teeth, and the bicuspids and molars are called the posterior teeth. The shape of the anterior teeth is generally the same for the upper and lower dental arch, with the top set generally being larger. The posterior teeth are of generally the same size and shape in both the upper and lower dental arches.

As used herein, "adjoining soft tissue" means the tissue surrounding the tooth structure, including the marginal gingiva, gingival sulcus, inter-dental gingiva, and the gingival gum structure on the lingual and buccal surfaces up to and including the muco-gingival junction and the pallet.

Referring now to the drawings, wherein reference numerals refer to the same or similar elements throughout the several views, an embodiment of a non-custom dental guard is shown in FIGS. 1-11 and generally designated at 30. The dental guard 30 comprises a body 32, including a front band portion 34 interconnecting a right rear molar portion 36 and a left rear molar portion 38. The right rear and left rear molar portions 36, 38 are integral with and extend rearwardly from the front band portion 34. The dental guard 30 is generally U-shaped and is symmetric across a plane extending through the mid-point of the front band portion 34 and between the right rear and left rear molar portions 36, 38. The shape and curvature, as well as the size, of the dental guard 30 generally approximate the curvature of a human dental arch. The dental guard 30 is intended to fit over at least a portion of or, alternatively, substantially all of the teeth in a dental arch such that the dental guard is preferably a horseshoe-shape that generally matches a catenary arch. In one embodiment, the dental guard 30 may be sized and configured to fit a plurality of teeth in a lower dental arch. In another embodiment, the dental guard 30 may be sized and configured to fit a plurality of teeth in an upper dental arch. In both embodiments, the size, shape and material of the dental guard 30 allows the dental guard to readily fit differently sized or differently shaped dental arches in a wide range, regardless of the variety of sizes and shapes of the teeth.

The body 32 of the dental guard 30 includes a smooth continuous buccal-labial front wall 40, also referred to herein as the front side wall, and an upper wall 42, also referred to herein as the upper side wall. The upper side wall 42 extends laterally at a distinct angle downwardly and inwardly from the buccal-labial wall 40. The buccal-labial wall 40 and the upper wall 42 together form a tray-shaped body having an L-shaped transverse cross section with at least a portion of the front wall 40 and the upper wall 42 offset by an angle. The angle may be 90° or the angle may be greater than 90° or less than 90°. The angle between the buccal-labial wall 40 and the upper wall 42 may vary along the length of the body 32 of the dental guard 30.

The front band portion 34 of the dental guard 30 is curved in an arc to generally correspond to the curvature of the mandibular front teeth. The front band portion 34 is sized to at least partially cover a front surface and upper surfaces of the lower front teeth, including the incisors and canines. The front wall 40 in this portion of the dental guard 30 may be referred to as a labial wall. The inner surface 45 of the labial wall 40 is configured to engage and conform to the front surfaces of the anterior teeth when in use. The outer surface 46 of the labial wall 40 is smooth and may be in contact with the inside lower lip. The upper wall 42 of the front band portion 34 of the dental guard 30 extends over the top edge and upper surfaces of the lower front teeth.

A lower free edge 47 of the labial wall 40 of the front band portion 34 may terminate above the soft tissue or gum line. In this embodiment, the lower edge 47 can be contoured to follow the soft tissue line between the gums and the front lower teeth, but not overlie the soft tissue so that the front band portion extends downward but does not overlap any portion of the soft tissue or gums. Alternatively, the labial wall 40 may extend downwardly and cover a portion of the soft tissue or gums below the front teeth.

The right rear and left rear molar portions 36, 38 of the dental guard 30 each comprise a buccal portion of the buccal-labial front wall 40. The buccal wall 48 portion is generally smooth and extends continuously from the labial wall 40. As described above, the upper wall 42 extends laterally at a distinct angle downwardly and inwardly from an upper edge of the buccal wall 48. The right rear and left rear molar portions 36, 38 may terminate at distal ends which engage the teeth short of a third rearward molar.

The buccal wall 48 has an arcuate bottom free edge 51 configured so that the buccal wall 48 may be positioned below the soft tissue line so that the buccal wall contacts or overlaps a substantial portion of the soft tissue below the lower molars. The large radius curve toward the distal end of the buccal wall 48 prevents the lower edge 51 from digging into the sensitive soft tissue. Alternatively, the edge 51 of the buccal wall 48 may terminate at and follow a contour of the soft tissue line along the outer facing surface contour of the molars and not contact or overlap any soft tissue of the gums below the molars.

Figure 10:
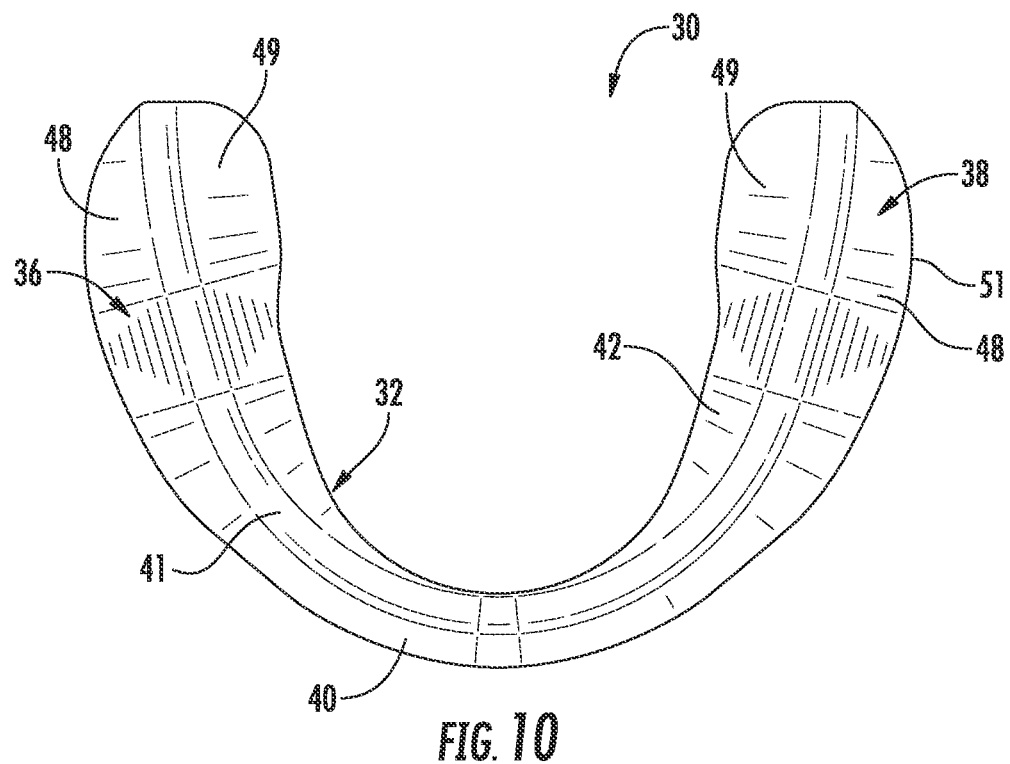
FIG. 10 is a top plan view of the dental guard as shown in FIG. 1.
Figure 11:
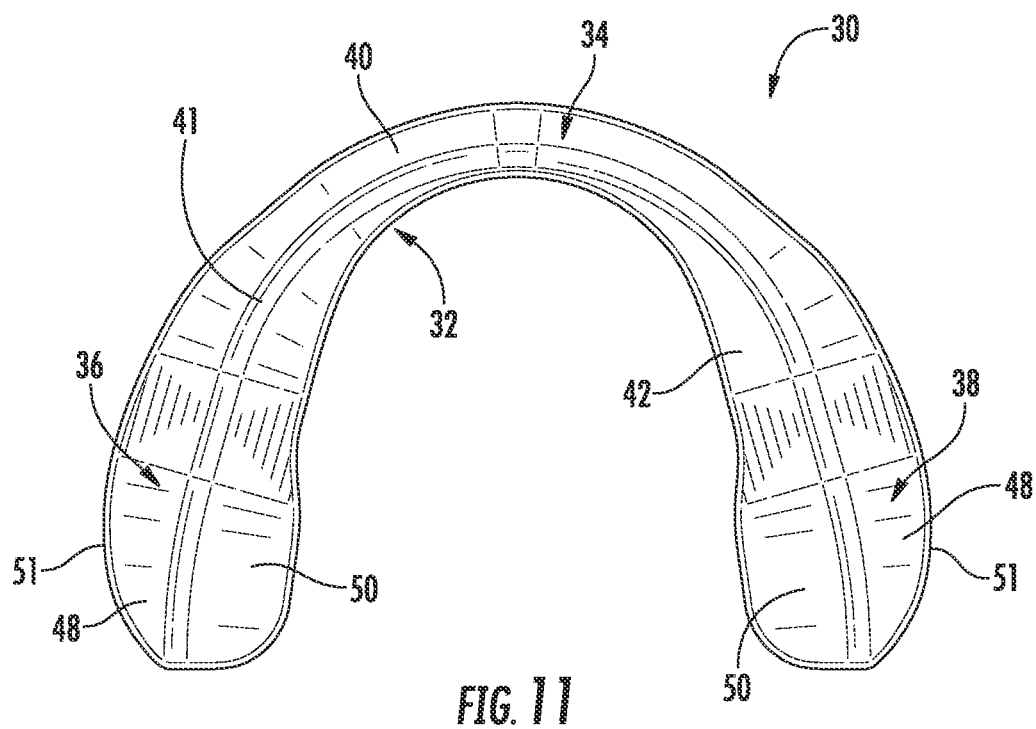
FIG. 11 is a bottom plan view of the dental guard as shown in FIG. 1.

The upper wall 42 of each of the rear molar portions 36, 38 form occlusal plates of the dental guard 30 in interocclusal regions configured to be disposed between the molars. The upper surface 49 and lower surface 50 of the interocclusal regions of the rear molar portions 36, 38 function as the occlusal plates engaged by the bottom facing side of the upper molars and the top facing side of the bottom molars, respectively. As best shown in FIGS. 10 and 11, the width of the upper wall 42 increases abruptly corresponding to a transition from the anterior teeth portion, which will be occupied by the incisors and canines, to the posterior teeth portion to be occupied by the bicuspids and molars. When the wearer installs the dental guard 30 in the mouth and bites down on the dental guard 30, the dental guard 30 will conform to the teeth surfaces. The upper and lower jaws and teeth will register with one another at their correct natural or voluntary bite position, and thus be in the most natural and comfortable alignment. Thus, the dental guard 30 provides significant interocclusal protection while significantly reducing the size, material usage, and negative impact of wearing a larger appliance in the mouth.

The dental guard 30 can be fabricated from any suitable material, such as a moisture resistant polymer or plastic material. In one embodiment, the dental guard is a one-piece molded device formed with a flexible and resilient plastic such as a thermoplastic elastomer, for example polyvinyl chloride, silicones, and other plastics and polymers and blends thereof. Suitable commercially available materials for the dental guard 30 include an ethylene-vinyl acetate copolymer resin available from DuPont under the name Elvax, Elvaloy from Dow, and Vistamaxx from Exxon. Examples of other materials that can be used to form the dental guard include, but are not limited to, polyolefins, wax, metal foil, paraffin, ethylene-vinyl acetate copolymer (EVA), ethylene-vinyl alcohol copolymer (EVAL), polycaprolactone (PCL), polyesters, polycarbonates, polyamides, polyurethanes, or polyesteramides. Examples of suitable polyolefins that can be uses to make the dental guard include, but are not limited to, polyethylene (PE), high density polyethylene (HDPE), low density polyethylene (LDPE), ultra low density polyethylene (ULDPE), polypropylene (PP), and polytetrafluoroethylene (PTFE) (e.g., TEFLON). An example of a suitable polyester for use in making the dental guard includes, but is not limited to, polyethylene terephthalate (PET), an example of which is MYLAR, sold by DuPont. An example of a suitable polyurethane barrier material is a polyurethane film manufactured by ArgoTech, which is located in Greenfield, Mass. In some embodiments, the dental guard can also be made from more than one material, such as in a dual moldings process, comprising a polymeric blend or multiple layers comprising two or more of the foregoing materials. For example, the dental guard is formed with a laminate having a soft surface and a tougher inner layer. Plasticizers, flow additives, and fillers known in the art can be used as desired to modify the properties of any of the foregoing polymers used to form the dental guard. It is understood that the dental guard as described herein is not intended to be limited to use of any particular material.

The dental guard 30 may be injection molded, vacuum formed, cut, or stamped from a sheet of the suitable material, such as a polymeric material. A manufacturing method is preferred that provides smooth, rounded edge surfaces as opposed to sharp, angled surfaces since smooth edges contribute to the overall comfortable feel of the dental guard 30.

The dental guard 30 may be sufficiently sturdy and dimensionally stable so as to assume and maintain a particular shape prior to use. At the same time, the walls 40, 42 of the dental guard 30 are quite thin. In general, the wall thickness of the dental guard 30 can be selected to yield a dental guard having a desired level of a combination of strength, rigidity, resilience, and flexibility. In order for the dental guard to be sufficiently resiliently flexible so as to conform to the teeth as result of dental compression, the dental guard will preferably have a thickness ranging from about 0.2 mm to about 4 mm, more preferably in a range of about 0.4 mm to about 2 mm, and most preferably in a range of about 0.6 mm to about 0.9 mm. The dental guard 30 cannot be so thin as to fail to retain its general shape after application of pressure, and cannot be so thick as to resist deformation. The dental guard 30 is suitable for use as a bruxism guard despite the thin walls, which provide protection to the teeth. As wall thickness increases, the dental guard 30 can become less comfortable and interferes with the normal relaxed position of the occlusal tooth surfaces when wearing the dental guard. An overly thick dental guard will be too stiff and fail to conform to the varying sizes of the dental arch among users.

The dental guard 30 is of sufficient length so that the front wall 40 covers at least the front or outer surfaces of the teeth in a human lower dental arch. For a dental guard 30 designed to fit the lower dental arch, a suitable overall length is from about 4 cm to about 6 cm. and the upper wall 42 is of sufficient width to extend over the crowns of the teeth in the lower dental arch. A suitable average width is from about 1 cm to about 2 cm. As described above, the width of the upper wall 42 increases for the posterior teeth. The broadest span of the dental guard 30 is about 60 mm between the buccal walls 48 of the right rear and left rear molar portions 34, 36. This is slightly larger than the largest span of a typical lower dental arch for reasons described below. It is understood that the dental guard 30 is intended to fit a range of differently sized dental arches, and that the dental guard 30, in use, conforms to fit the dental arch of a particular user. Therefore, the dimensions presented herein are not intended to be limiting, but are rather presented as a guide for constructing the dental guard 30. For example, dental guards designed for use in children or smaller adults are proportionally smaller than those described above for the normal adult.

Figure 12:
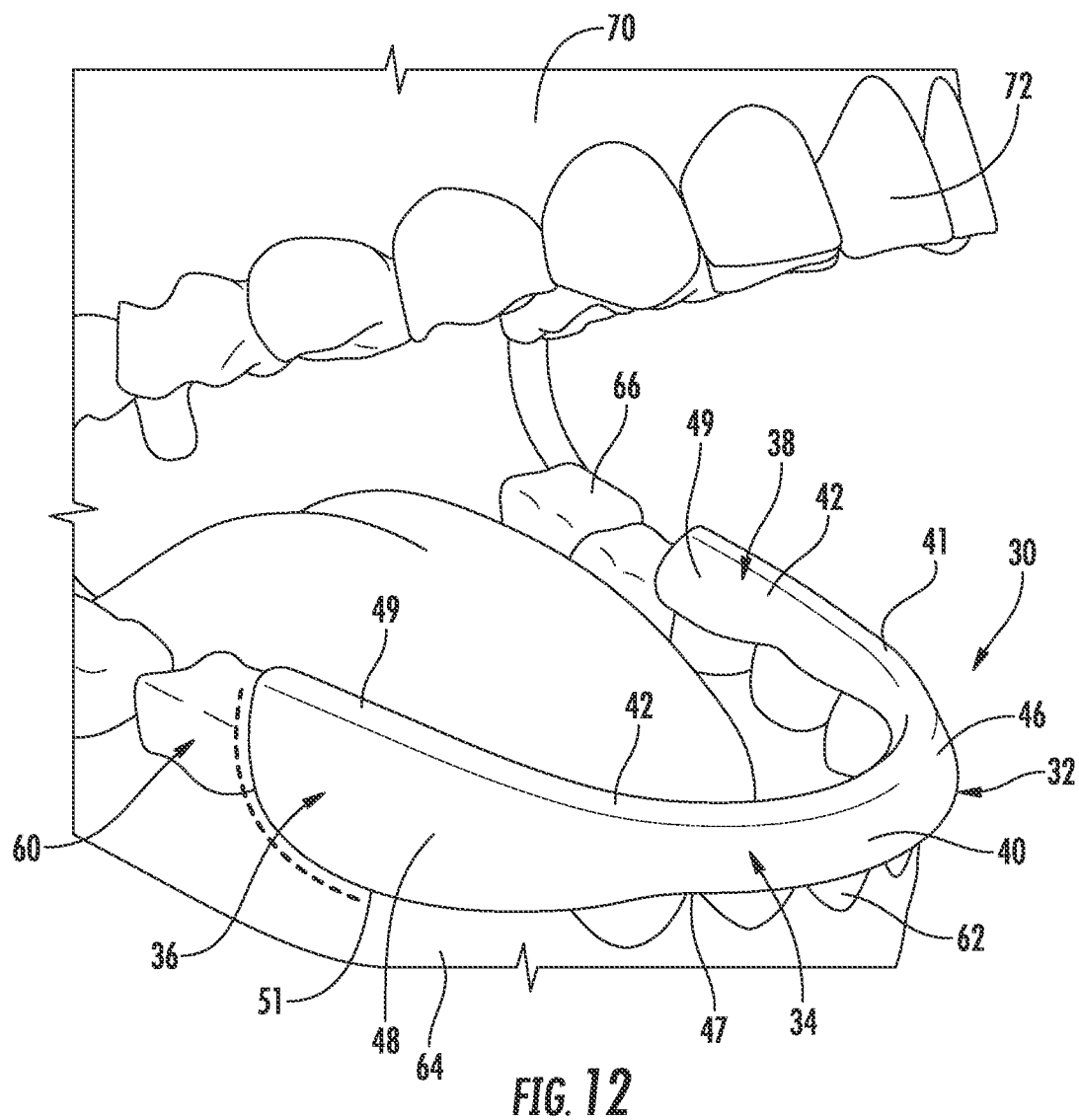
FIG. 12 is a front right side perspective view of the dental guard as shown in FIG. 1 in position on a lower dental arch with jaws open.
Figure 13:
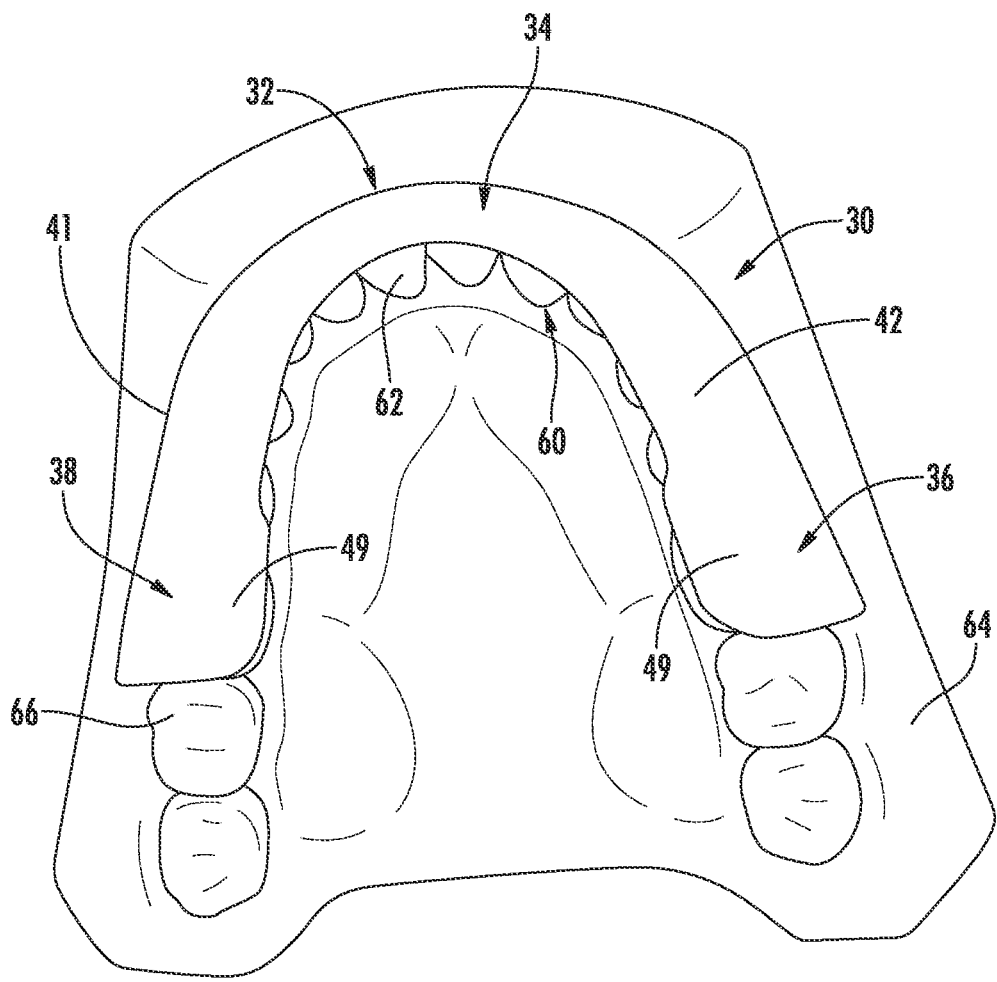
FIG. 13 is a top plan view of the dental guard in position on the lower dental arch as shown in FIG. 12 with jaws closed and showing only the lower jaw.

The dental guard 30 is worn to reduce symptoms and protect against damage caused, for example, by bruxism. Referring to FIGS. 12-17, in one embodiment, the user first positions the dental guard 30 over the teeth 62 of the lower dental arch 60. The user places the dental guard 30 onto the teeth 62 such that the curved front band portion 34 and the right and left rear molar portions 36, 38 extend along and around surfaces of the teeth (FIGS. 12 and 13). The dental guard 30 is generally centered on the midline of the mandibular jaw 64 and the labial wall 40 covers the first five teeth on each side of the midline. The labial wall 40 conforms to the general shape and contour of the outer surfaces of the anterior teeth. For a typical wearer, the surfaces of the teeth 62 that contact and are conformed to by the labial wall 40 are the four incisor teeth, the two canine teeth and the two premolar teeth on each side.

Figure 14A:
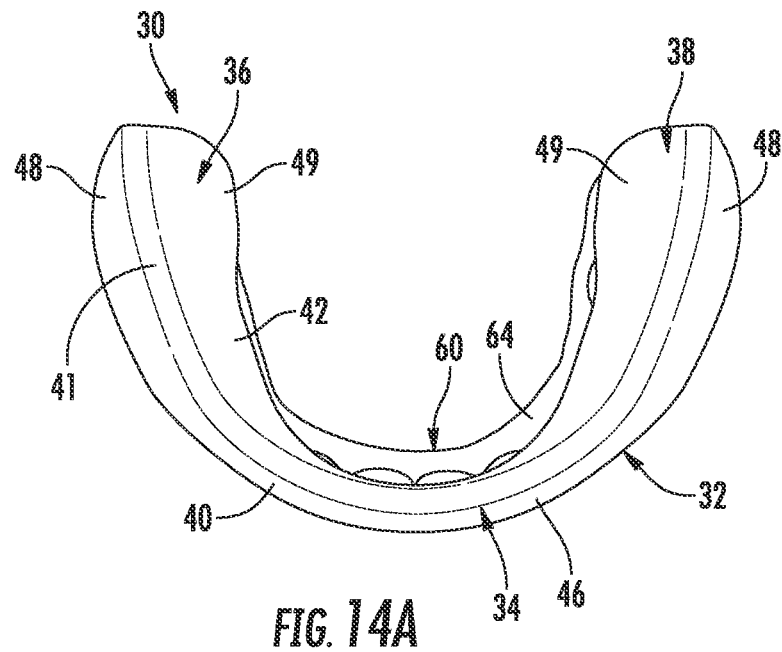
FIG. 14A is a top plan view of the dental guard in position on the lower dental arch as shown in FIG. 13 with jaws open showing only the lower jaw.
Figure 14B:
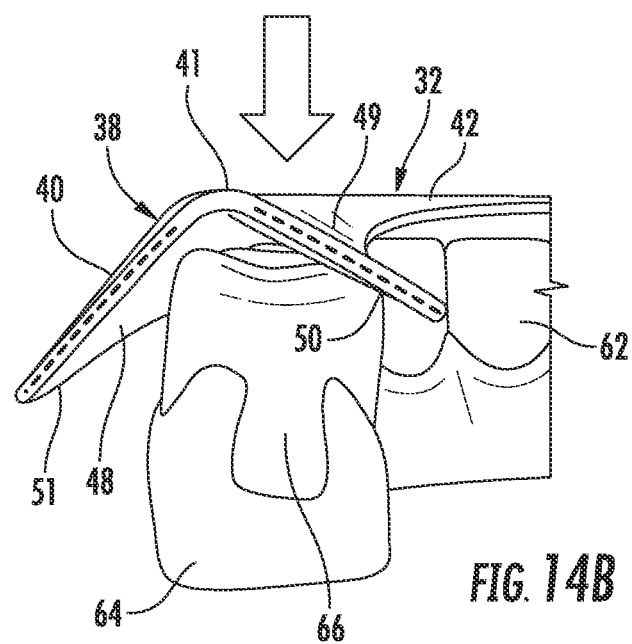
FIG. 14B is a rear left side perspective view of a portion of the dental guard in position on a portion of the lower dental arch as shown in FIG. 14A.
Figure 15A:
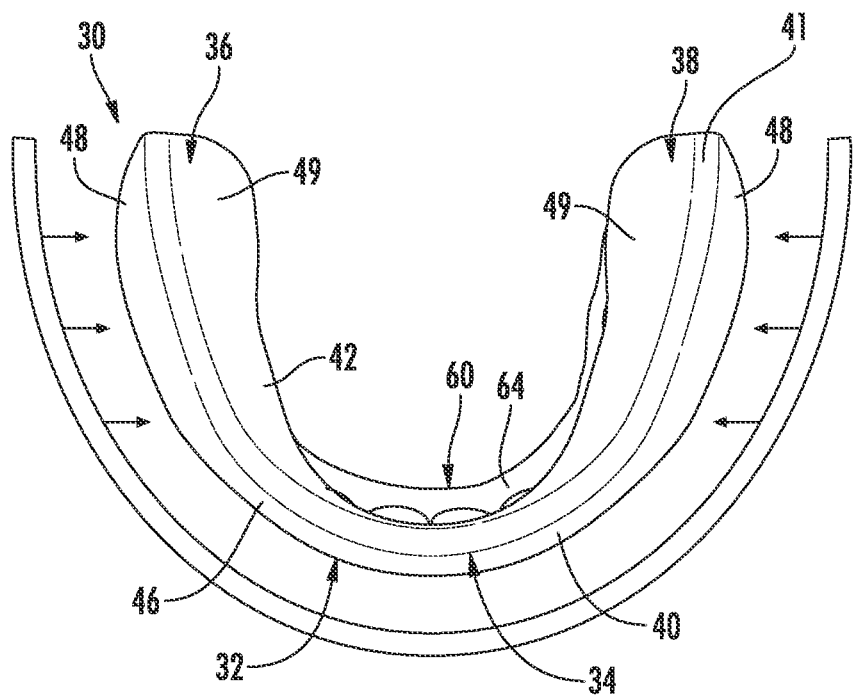
FIG. 15A is a top plan view of the dental guard in position on the lower dental arch as shown in FIG. 13 with jaws closed showing only the lower jaw.
Figure 15B:
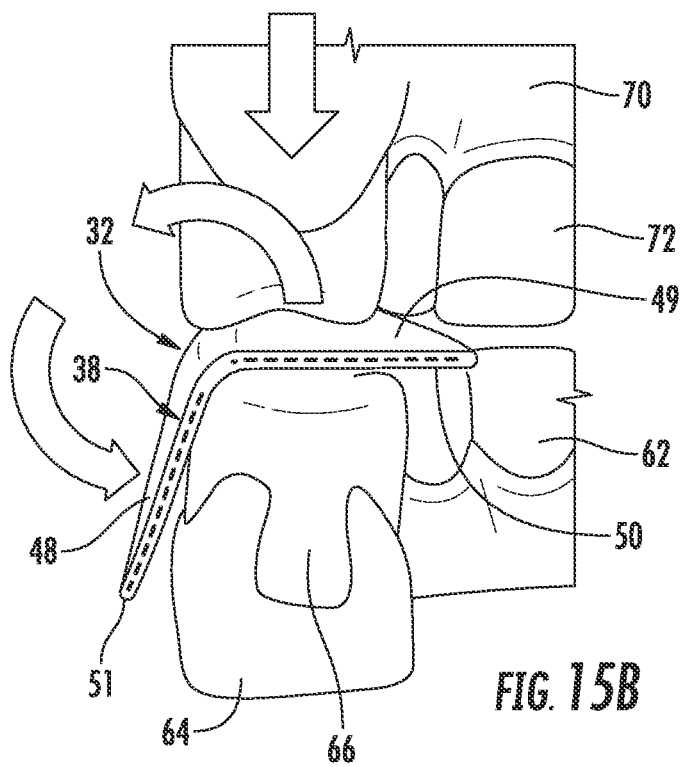
FIG. 15B is a rear left side perspective view of a portion of the dental guard in position on a portion of the lower dental arch as shown in FIG. 15A.
Figure 16:
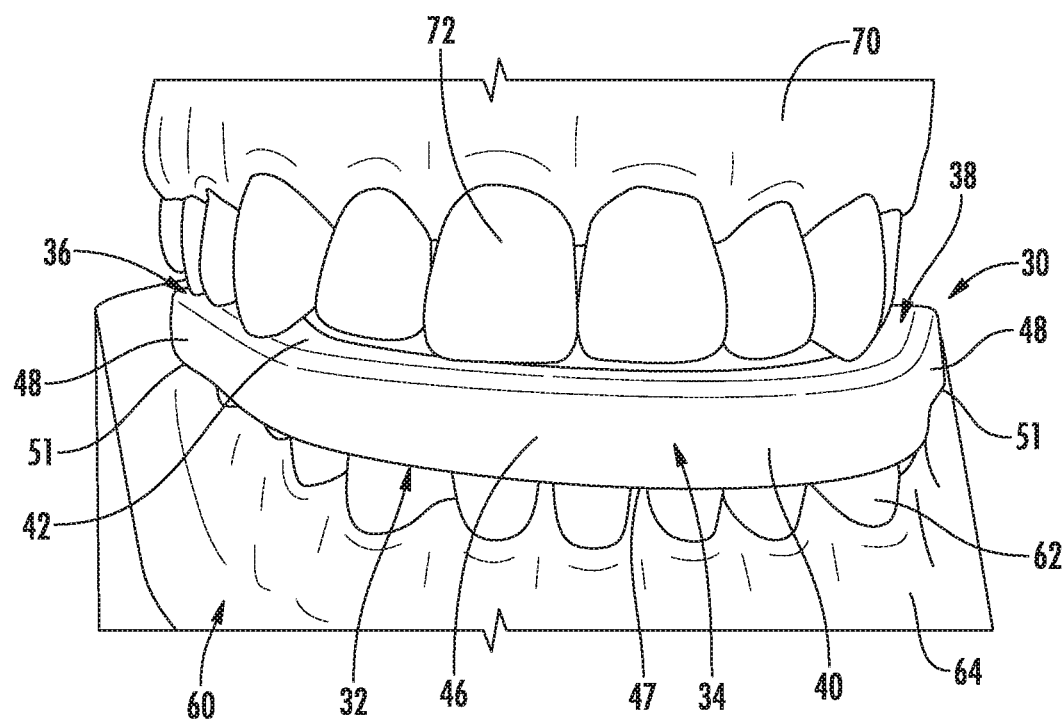
FIG. 16 is a front perspective view of an upper jaw and a lower jaw with the dental guard as shown in FIG. 1 in position on the lower dental arch with the jaws closed.

FIGS. 14A and 14B show the position of the dental guard 30 on the lower arch 60 with the jaws 64, 70 open. The buccal wall 48 and the upper wall 42 of the right rear and left rear molar portions 36, 38 engage the occlusal edges of the molars 66. As seen in FIG. 14A, the width of the dental guard 30 is wider than the lower dental arch 60. The resilience of the dental guard 30 biases the dental guard 30 outwardly and its dimensional stability maintains this position on the teeth 62. The angled buccal wall 48 and upper wall 42 allow the buccal wall 48 to rotate when compressed between the occlusal surfaces of the teeth by dental pressure as the lower jaw 64 and upper jaw 70 close on the upper wall 42 as indicated by the arrow in FIG. 14B. As shown in FIGS. 15A and 16, when the lower teeth 62 and the upper teeth 72 come together with normal dental pressure, the buccal wall 48 of the dental guard 30 rotates outwardly and downwardly as indicated by the arrows in FIG. 15B. The inner lip and cheek surfaces orient the buccal wall 48 to lay alongside the outside surfaces of the teeth 62 and gums rather than being forced directly downward into the gum line. The buccal wall 48 readily conforms to the surface of the posterior lower teeth and adjoining soft tissue. The upper wall 42 of the dental guard is forced down between the occlusal tooth surfaces during use. The dental guard 30 is accommodated by reason the shape and the inherent flexibility and resiliency of the material, which readily deforms to conform to the varying contours, sizes and the irregularities of the teeth 62 among a wide variety of dental arches. The resiliency of the dental guard 30 causes the walls 42, 48 to engage the teeth providing gripping action through cooperation of the walls 42, 48 and facilitating retention of the dental guard 30 on the teeth.

Figure 17:
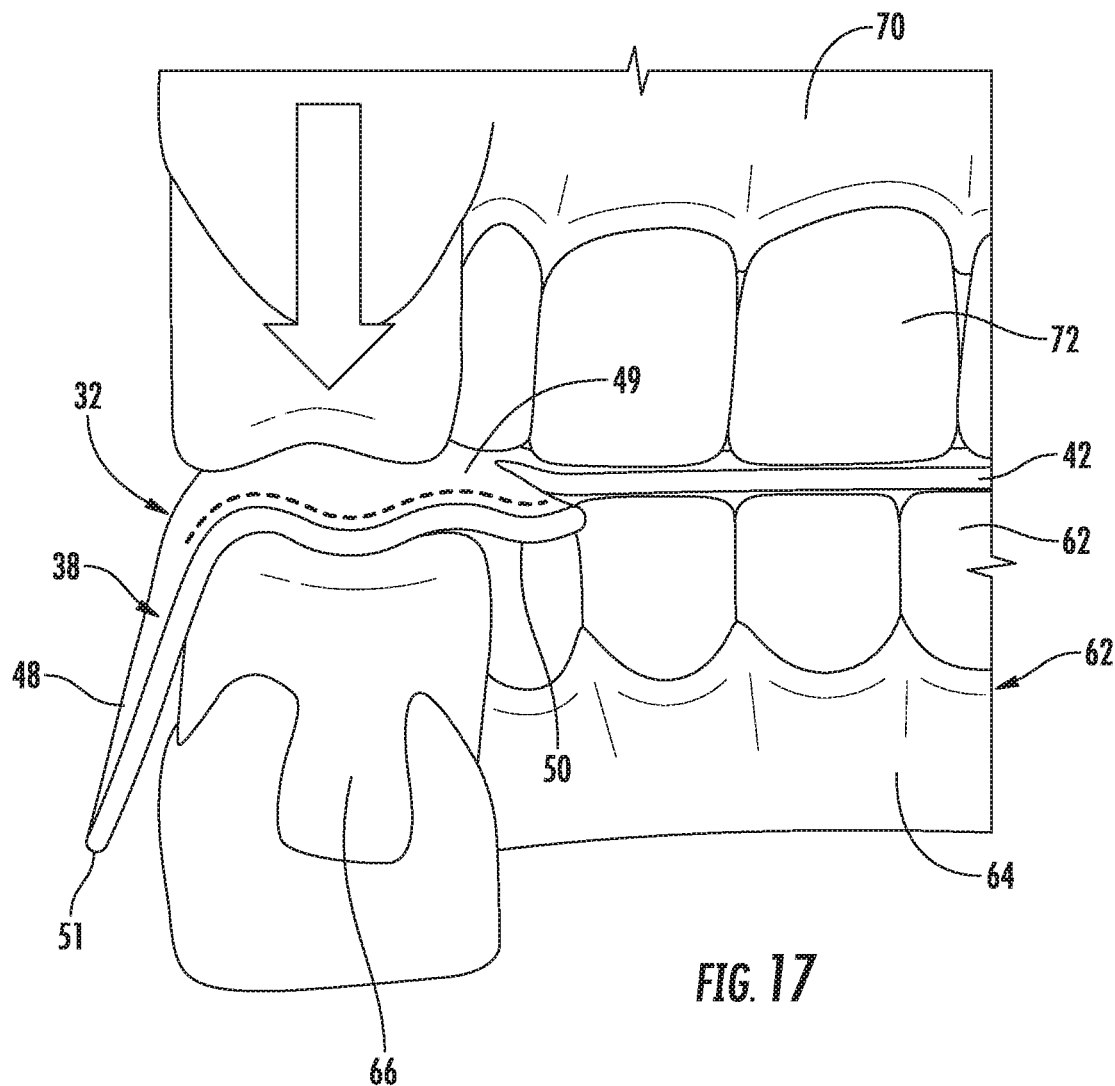
FIG. 17 is a rear elevation view of a portion of the dental guard in position on the lower dental arch as shown in FIG. 16 with the jaws closed.

As shown in FIG. 17, the occlusal regions of the right and left rear molar portions 36, 38 of the dental guard 30 between the upper molars 72 and the lower molars 62 act to cushion compressive forces between the upper and lower molars with a resistive force. Compression, deflection or deformation of the dental guard 30 may occur in response to the compressive forces because of, for example, the properties of the materials from which the dental guard is made and because of the geometry of the dental guard. The bite area of the occlusal plates adapts to the contours of the molars when compressed. Moreover, the lower jaw 64 and the upper jaw 70 can still move side to side relative to one another when biting down. The occlusal regions of the dental guard 30 only temporarily deform under dental pressure and return to their original uncompressed shape when the compressive forces are removed. As described and shown herein, the occlusal surface of the upper wall 48 of the dental guard 30 corresponds to the crowns of the teeth 62 and is wider at the molars 72 to minimize the possibility of the tongue dislodging the dental guard 30. The absence of a lingual wall provides a universal fit and further reduces tongue contact.

The dental guard 30 is designed to be worn overnight while a person is sleeping. Due to the comfortable fit of the dental guard 30, it is possible to wear the dental guard 30 for extended periods of time, as desired. Typical durations may last from about 2 hours to about 12 hours. To remove the dental guard 30 after the desired time period, the user simply grasps a corner or portion of the dental guard and pulls the dental guard off the teeth.

Figure 18:
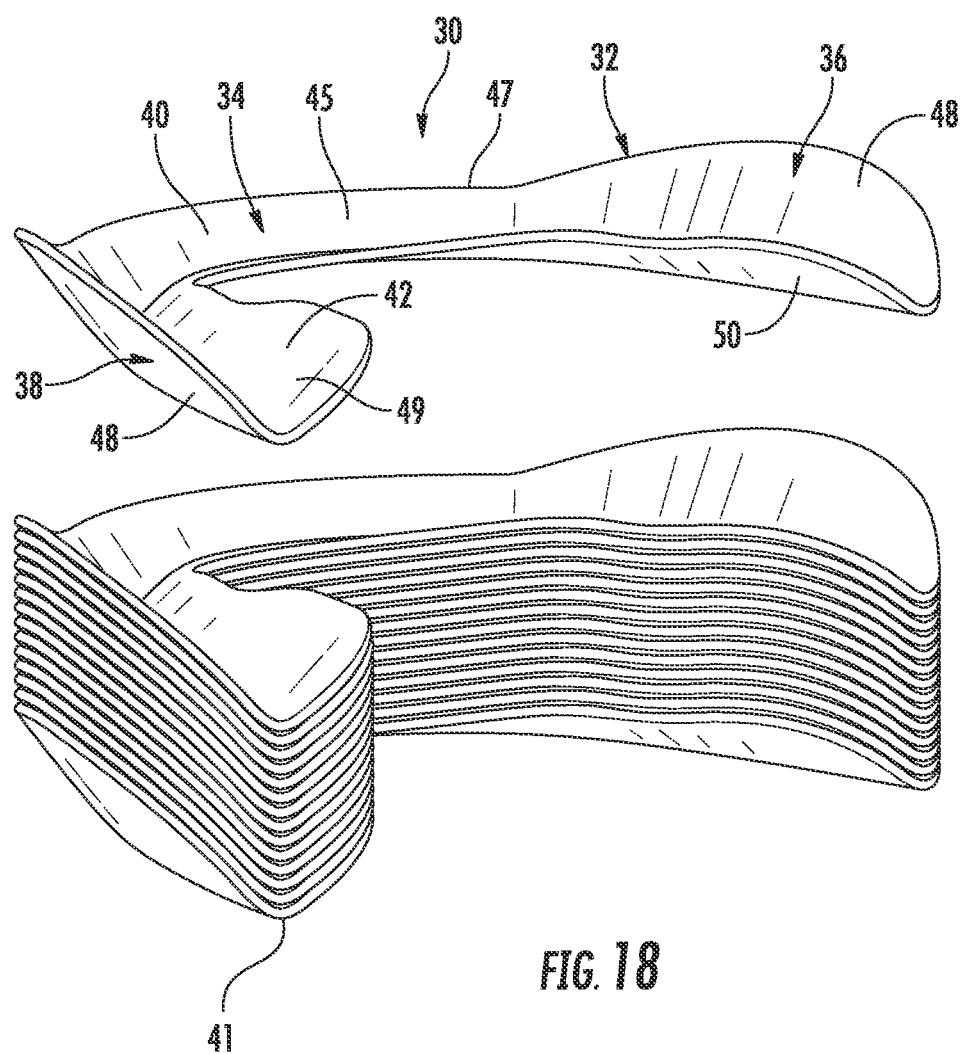
FIG. 18 is a rear perspective view of a plurality of stacked dental guards as shown in FIG. 1.

The dental guard 30 may be provided to the user substantially ready for placement on the teeth. The dental guard 30 can be packaged by any means suitable for containing and transporting the dental guard to the consumer. For convenience, a plurality of dental guards 30 may be packaged together. To efficiently utilize the space within a kit package, the configuration of the dental guard 30 allows a plurality to be stacked, nesting together within a package in one stack (FIG. 18) or multiple stacks. The angled walls 40, 42 of the dental guard provides a substantially planar single edge 41 at the intersection of the walls that provides dimensional stability and resists warping or twisting when resting on a flat surface or when nested with one another. As a result, the stacks are uniform and stable. The forces between the dental guards are balanced and do not compress or splay lower dental guards 30 in the stack. Further, the larger occlusal regions of the dental guard 30 allow ease of handling by suction stacking equipment. Alternatively, it is understood that each dental guard 30 may be sealed individually, as desired, in a single use package.

The dental guard 30 as described herein has many advantages, including comfortably fitting dental arches of different sizes and curvatures and a wide range of differently sized or shaped teeth corresponding to different people. The dental guard 30 is substantially devoid of structures corresponding to the size and shape of a person's unique dentition. The thin flexible dental guard 30 maximizes retentive fit while reducing obstruction in the wearer's airway, reducing distraction to the user wearing the device, and increasing overall comfort for the wearer. The absence of a lingual wall reduces the chance of pharyngeal reflex since tongue contact with the dental guard 30 is minimal. The absence of a lingual wall also allows the tongue to lay flat which improves comfort and opens the airway for breathing or talking, both of which encourage compliance.

Since there is no material covering the inner surface of the teeth, there is less obstruction between the tongue and the dental guard during use, opening the airway and increasing comfort. The dental guard as disclosed herein uses significantly less material, eliminates this uncomfortable rear obstruction in the wearer's mouth, is much less intrusive so as to be less of a distraction to the wearer, and opens the airway for the user while wearing the device.

Although the dental guard has been shown and described in considerable detail with respect to only a few exemplary embodiments thereof, it should be understood by those skilled in the art that we do not intend to limit ourselves to the embodiments since various modifications, omissions and additions may be made to the disclosed embodiments without materially departing from the novel teachings and advantages of the apparatus, particularly in light of the foregoing teachings. For example, the dental guard 30 may be sized and configured to correspond to either an upper or lower dental arch, as the lower dental arch is typically smaller than the upper arch, with lower teeth that are typically smaller than the upper teeth. It is also within the scope of this description to provide varyingly-sized dental guards to account for significant variability among different people's dental arches or teeth, such as adults versus children. Accordingly, we intend to cover all such modifications, omission, additions and equivalents as may be included within the spirit and scope of the apparatus, system and method as defined by the following claims. In the claims, means-plus-function clauses are intended to sticker the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

We claim:

1. A dental guard for treatment of bruxism in a human dental arch having a width and including a plurality of anterior teeth and posterior teeth having outer surfaces and occlusal surfaces, the dental guard comprising:

an elastically deformable body formed from a flexible resilient material and having a front band portion, and a pair of molar portions contiguous with and extending from ends of the front band portion to distal ends of the pair of molar portions, the front band portion and the pair of molar portions of the body forming a U-shape, the body including a front side wall having a smooth inner surface and a longitudinal edge, wherein the body is planar along the longitudinal edge of the front side wall, and an upper side wall having a smooth inner surface, the upper side wall extending at an angle from the longitudinal edge of the front side wall such that prior to use the longitudinal edge defines a first angle between the inner surface of the front side wall and the inner surface of the upper side wall, wherein a distance between the longitudinal edge of the front side wall at the distal ends of the pair of molar portions is dimensionally stable in a plane including the longitudinal edge of the front side wall and is configured to differ from the width of the human dental arch, wherein when the jaws are open the body is adapted to be positioned to fit over the plurality of teeth in the human dental arch such that the inner surfaces of the front wall and the upper wall engage the occlusal surfaces of the posterior teeth, wherein when the jaws are closed the body flexes such that the longitudinal edge defines a second angle between the inner surface of the front side wall and the inner surface of the upper side wall, and the molar portions rotate in the plane for at least partially conforming the front side wall to the outer surfaces and the upper side wall to the occlusal surfaces of differently sized and differently shaped teeth corresponding to different people during use, and wherein the angle defined by the longitudinal edge between the inner surface of the front side wall and the inner surface of the upper side wall returns to the first angle upon removal of the body from the dental arch.

2. The dental guard as recited in claim 1, wherein a portion of the front side wall corresponding to the front band portion is a labial wall adapted to be disposed between the outer surfaces of the anterior teeth and the inside surface of the lip.

3. The dental guard as recited in claim 2, wherein the front side wall of each of the pair of molar portions comprises a buccal wall contiguous with the labial wall, the buccal wall adapted to be disposed between the outer surfaces of the posterior teeth and inside surfaces of the cheeks.

4. A dental guard as recited in claim 3, wherein the buccal wall is adapted to overlap a junction of a person's gingival margin and gum line during use.

5. The dental guard as recited in claim 2, wherein the labial wall terminates in a longitudinal free edge adapted to be positioned adjacent a gingival margin during use.

6. The dental guard as recited in claim 1, wherein the dental arch comprises a lower dental arch and the teeth are lower teeth.

7. The dental guard as recited in claim 1, wherein the dental arch comprises an upper dental arch and the teeth are upper teeth.

8. The dental guard as recited in claim 1, wherein the distance between the longitudinal edge of the front side wall at the distal ends of the pair of molar portions configured is less than the width of the human dental arch.

9. The dental guard as recited in claim 1, wherein the distance between the longitudinal edge of the front side wall at the distal ends of the pair of molar portions configured is greater than the width of the human dental arch.

10. A dental guard as recited in claim 1, wherein the body has a thickness of about 0.2 mm to about 4 mm.

11. A dental guard as recited in claim 1, wherein the body has a thickness of about 0.4 mm to about 2 mm.

12. A dental guard as recited in claim 1, wherein the body has a thickness of about 0.6 mm to about 0.9 mm.

13. A dental guard as recited in claim 1, wherein the body has a thickness of less than about 1.0 mm.

14. The dental guard as recited in claim 1, wherein the upper side wall of each molar portion comprises a generally planar occlusal plate having a top and a bottom surfaces, the occlusal plates adapted to be positioned between occlusal surfaces of upper teeth and lower teeth to absorb forces when the jaws are clenched.

15. The dental guard as recited in claim 1, wherein the upper side wall of the pair of molar portions has a width of about 8 mm in a direction generally perpendicular to longitudinal axis of the front wall.

16. A dental guard as recited in claim 1, wherein the body has a transverse cross section that is approximately V-shaped for receiving the teeth.

17. A dental guard as defined in claim 1, wherein the upper side wall has a width increasing from the front band portion to the molar portions.

18. A dental guard as defined in claim 1, wherein the body has a length and a width, the length and width of the body adapted to extend along the dental arch to cover the outer surfaces and crowns of the teeth in the dental arch to the distal end of the second molar of the lower dental arch.

19. A kit for use in protecting a person's teeth, the kit comprising a plurality of the dental guards according to claim 1.

20. A method for protecting against effects of bruxism in a human dental arch having a width and including a plurality of anterior teeth and posterior teeth having outer surfaces and occlusal surfaces, the bruxism protection method comprising the steps of:
- a) providing an elastically deformable body formed from a flexible resilient material and having a front band portion, and a pair of molar portions contiguous with and extending from ends of the front band portion to distal ends of the pair of molar portions, the front band portion and the pair of molar portions forming a U-shape, the body including
  - a front side wall having a smooth inner surface and a longitudinal edge, wherein the body is planar along the longitudinal edge of the front side wall, and
  - an upper side wall having a smooth inner surface, the upper side wall extending at an angle from the longitudinal edge of the front sidewall such that prior to use the longitudinal edge defines a first angle between the inner surface of the front side wall and the inner surface of the upper side wall, wherein a distance between the longitudinal edge of the front side wall at the distal ends of the pair of molar portions is dimensionally stable in a plane including the longitudinal edge of the front side wall and is configured to differ from the width of the human dental arch;
- b) placing the body over the plurality of teeth in the human dental arch such that the inner surfaces of the front wall and the upper wall engage the occlusal surfaces of the posterior teeth;
- c) conforming the body to the teeth and surrounding tissue by dental pressure so that when the jaws are closed the body flexes such that the longitudinal edge defines a second angle between the inner surface of the front side wall and the inner surface of the upper side wall, and the molar portions rotate in the plane and at least partially conforms to the outer and occlusal surfaces of differently sized and differently shaped teeth corresponding to different people during use; and
- d) removing the body from the dental arch wherein the angle defined by the longitudinal edge between the inner surface of the front side wall and the inner surface of the upper side wall returns to the first angle.

21. The bruxism protection method as recited in claim 20, wherein the dental arch comprises a lower dental arch and the teeth are lower teeth.

22. The bruxism protection method as recited in claim 20, wherein the dental arch comprises an upper dental arch and the teeth are upper teeth.

23. The bruxism protection method as recited in claim 20, wherein the distance between the longitudinal edge of the front side wall at the distal ends of the pair of molar portions is less than the width of the human dental arch.

24. The bruxism protection method as recited in claim 20, wherein the distance between the longitudinal edge of the front side wall at the distal ends of the pair of molar portions is greater than the width of the human dental arch.

* * * * *